United States Patent [19]
Riley

[11] Patent Number: 5,792,421
[45] Date of Patent: Aug. 11, 1998

[54] NON-INTRUSIVE MICROWAVE DECONTAMINATION OF INFECTIOUS WASTE

[75] Inventor: Brian Riley, Willimantic, Conn.

[73] Assignee: MicroSterile Safe Corporation, Willimantic, Conn.

[21] Appl. No.: 506,071

[22] Filed: Jul. 24, 1995

[51] Int. Cl.$^6$ .................................................. A61L 2/00
[52] U.S. Cl. .................... 422/21; 219/679; 219/762; 250/455.11; 422/186; 422/307; 588/227; 588/258
[58] Field of Search ............ 422/21, 186, 307; 250/492.1, 455.11; 219/762, 679; 588/227, 258

[56] References Cited

U.S. PATENT DOCUMENTS

| | | |
|---|---|---|
| 5,019,359 | 5/1991 | Kutner et al. .................... 422/21 X |
| 5,035,858 | 7/1991 | Held et al. ......................... 422/21 |
| 5,084,243 | 1/1992 | Wijts ................................ 422/26 |
| 5,124,125 | 6/1992 | Brent ............................... 422/21 |
| 5,213,758 | 5/1993 | Kawashima et al. .............. 422/21 |
| 5,223,231 | 6/1993 | Drake ............................. 422/21 |
| 5,270,000 | 12/1993 | Goldner et al. .................. 422/21 |
| 5,348,235 | 9/1994 | Pappas ............................ 422/21 |
| 5,413,757 | 5/1995 | Kutner et al. .................... 422/21 |

FOREIGN PATENT DOCUMENTS

| | | | |
|---|---|---|---|
| 0410306 | 1/1991 | European Pat. Off. .................. 422/21 |
| 9115247 | 10/1991 | WIPO ........................................ 422/21 |

Primary Examiner—Krisanne Thornton
Attorney, Agent, or Firm—McCormick, Paulding & Huber

[57] ABSTRACT

In a method and apparatus for decontaminating biomedical waste, the waste is introduced with moisture into a flexible, polymeric bag defining an internal volume and having a bursting point in response to expansion of the internal volume. The waste and moisture is then sealed within the bag, and the sealed bag is introduced into a decontamination chamber and subjected to microwave radiation within the chamber at a predetermined level and time sufficient to sterilize the waste. The decontamination chamber defines an internal surface spaced a predetermined distance from the flexible bag with the bag at about ambient temperature. The predetermined distance is (i) large enough to permit expansion of the bag within the space when the bag is subjected to the microwave radiation, and (ii) small enough to permit the internal surface to engage the bag and thereby prevent further expansion of the bag prior to reaching its bursting point in order maintain the bag in its sealed condition throughout the microwaving and decontamination process.

17 Claims, 4 Drawing Sheets

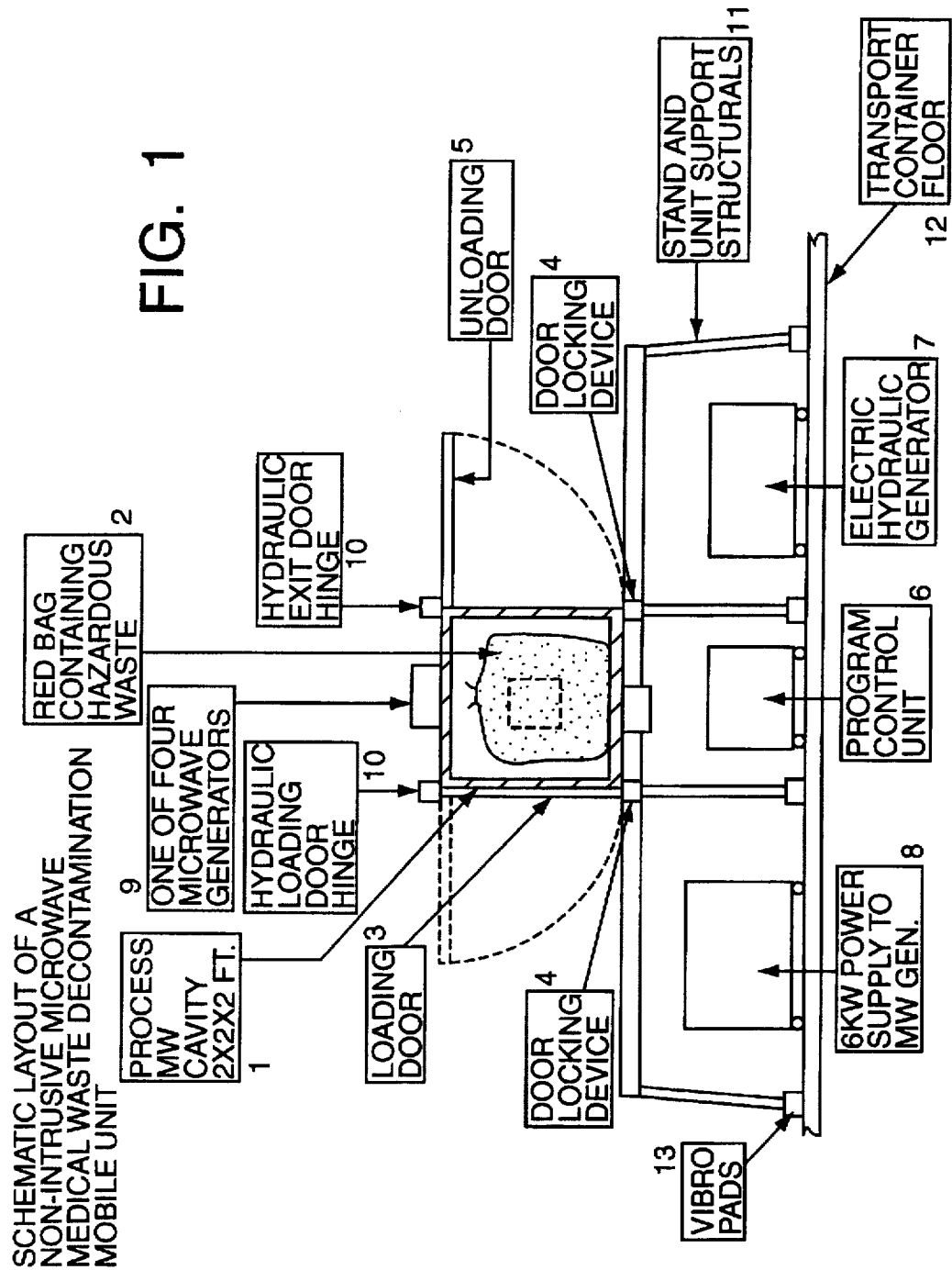

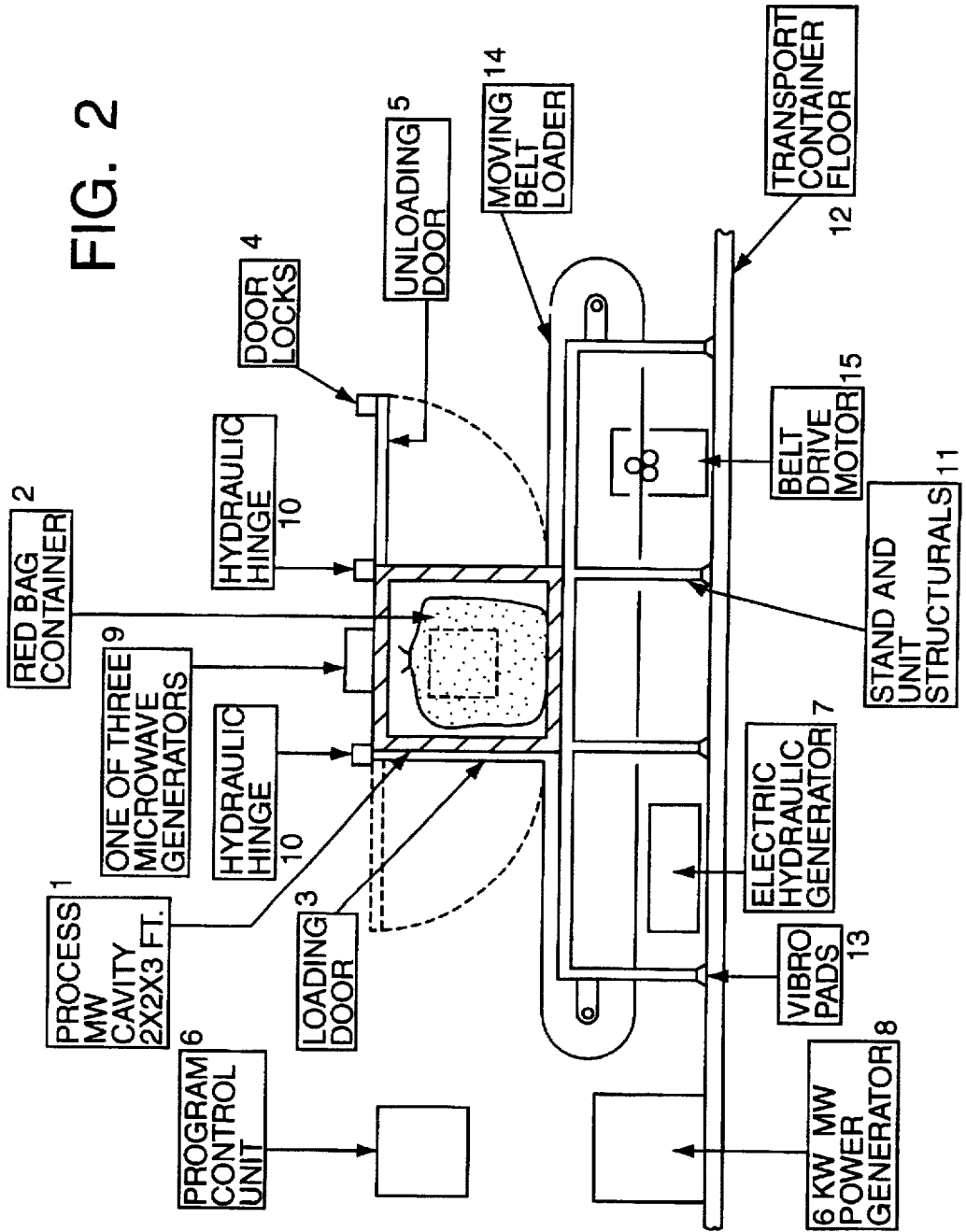

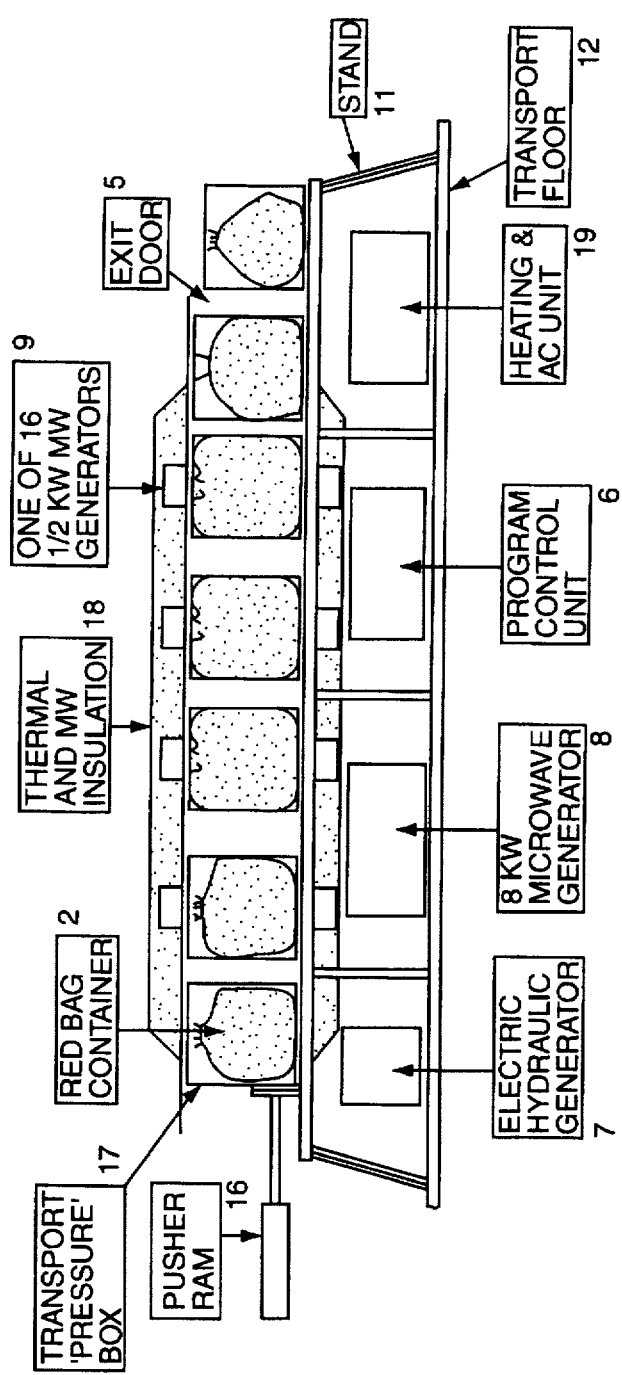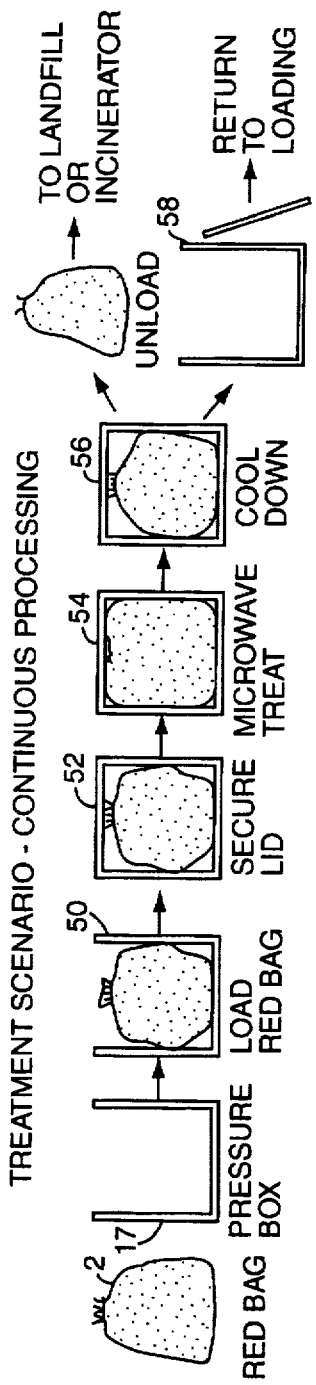

CONCEPTUAL DESIGN OF A ROTARY MICROWAVE
UNIT FOR THE DECONTAMINATION OF HAZARDOUS
MEDICAL WASTE

NON-INTRUSIVE MICROWAVE DECONTAMINATION OF INFECTIOUS WASTE

BACKGROUND OF THE INVENTION

Biomedical waste from medical facilities within the U.S. has been increasing from $3.7 billion in 1988 to over $12 billion in 1994. Infectious waste disposed of in red bags contains all of the possible by-products of socialized medicine, hospital management, dentists, physicians, morticians, and other allied originators.

Within these by-products will be the body fluids with attendant excreta of patients infected with bacteria such as HIV, Hepatitis B, Herpes, and variations and mutations of other potential lethal viruses and bacteria.

The acknowledgment of "smart" bacteria, i.e., bacteria which can learn from prior administered antibiotics, and mutate into more virulent forms, necessitates that all medical waste be sterilized or decontaminated prior to leaving the medical facilities or be incinerated as soon as possible.

However, the vast majority of medical red bags are disposed of by transportation over public roads and state highways. Proposed Environmental Protection Agency regulations are expected to address these issues, thus curtailing dangerous transportation of infectious waste upon public roadways and the process of incineration emissions.

With the continual rise in the volume of medical waste transported (by truck) along state and city thoroughfares, there is an increase in the likelihood of accidental spillage resulting in the spread of serious infectious contamination at the scene.

Many states have responded with regulations governing infectious waste packaging, hauling, transportations and off-site incineration or burial. Research laboratories, hospitals, physicians, medical centers, dentists, morticians, etc., will be faced with regulations and administrative costs to cover the disposal and tracking of their waste. They will also be responsible for the safety of the infectious waste in transit and at all stages after the red bag leaves the medical facility. Although the transporters must carry adequate insurance, the biowaste generator is not relieved of responsibility of liability for an outbreak of a disease if there is inadvertent contamination of a process worker or handler. Insurance costs follow the degree of liability of generated biohazardous waste.

Further complications in the safe disposal of infectious waste are associated with the handling and processing stages. Moreover, personnel and equipment operators require their diligence throughout this process.

To minimize the above-mentioned dangers, the present invention proposes herein that the red bag and its infectious contents per se be processed "in situ" without opening or shredding the bag. To achieve this, the present invention has designed and constructed a microwave decontamination system capable of processing red bags at a generator's site prior to transportation to an offsite incinerator or landfill.

Occupational Safety and Health Administration (OSHA) has outlined rules and procedures for the processing of infectious waste.

Decontamination of the contents of a red bag i.e., patients' garments, sheets, diapers, gloves, gauzes, needles, scalpel blades, suture needles, etc. at hospitals, has been extended to cover infectious waste from small generators such as physician's health centers, dentists, morticians and others.

With the continued rise in the number of cases of HIV, Hepatitis, and Herpes, and once considered eradicated diseases such as tuberculosis and variations and mutations of the above, there is an increasing need to prevent or contain all variants of infectious materials.

Accordingly, it is an object of this invention to provide a system which will provide a completely decontaminated waste product, ready for pickup by routine waste haulers directly to the disposal site.

It is further proposed to provide to health care organizations a mobile or transportable system which will process their infectious red bag waste directly on-site.

Others have responded to the problem by processing infectious waste on site by first shredding and then disinfecting with chlorine dioxide ($ClO_2$) (Mediclean IWP.1000) or by multichamber incineration (Brunner & Brown) or by autoclaving or by steam sterilization (AMSCO) or by hydropulping (Medical Safe TEC). A variation of the mechanical-disinfection and microwave treatment has been developed (Vetco-Sanitec & ABB-Sanitec). All of these procedures and systems contain within their process the disadvantage that at some stage, the red bag is violated by shredding and its contents exposed to the environment. Should a malfunction of the electrical or mechanical system occur, the machine and its enclosure are exposed to the infectious and hazardous contents of the container.

The decontamination of the inside of shredders and hammer mills, while in the contaminated state, is expensive at the least and dangerous to personnel at the best.

To solve the problem of on-site decontamination of infectious waste and also to protect the environment and operating personnel, the present invention proposes a non-intrusive method of processing.

SUMMARY OF THE INVENTION

It is thus an object of the present invention to provide a safe and economic processing system for the treatment of infectious waste by a procedure of non-intrusive microwave sterilization. The associated equipment, machines, times at temperature and microwave power requirements will be specified to achieve full and complete decontamination of an unopened red bag. According to the present invention, this objective is achieved thermally and by steam processing of the red bag and its infectious contents within an enclosed cavity. The thermal temperature of the steam pressure is generated within the cavity by microwave energy. The red bag is prevented from breaking by steam pressure by being enclosed within the walls of the microwave cavity.

Similarly, modifications to the basic design as shown diagrammatically (in FIGS. 3A and 4A), batch processing, can be increased to a continuous processing without disturbing the main idea or logic within the patent. To achieve continuous versus batch processing, the embodiment of the invention also includes low pressure boxes into which the red bag is placed prior to loading into the microwave oven (FIGS. 3A and 4A).

One system embodiment of the invention includes a microwave 'oven' cavity with loading and unloading doors, interlocking safety devices, microwave generators (magnetrons), a microwave power unit and programs.

Another embodiment of the invention employs a continuous moving bed loader and unloader.

Another embodiment of the invention is a fully continuous decontamination system in which the red bag is first placed in a pressure box and then push-loaded through a continuously heated microwave tunnel oven. Exiting the oven in decontaminated form, the biomaterial is microwaved and compacted and re-bagged in a green safe bag.

Yet another embodiment of the invention is a compacted version of the continuous decontamination system which employs a rotary oven. A pressure box, moving hearth, microwave cavity at fixed temperatures and power, and a green bag processed product are also included. The rotary processor using the same processing volume and power as the linear version will occupy a smaller space. The operator of this system will be at one end of the machine for loading and unloading rather than at both ends.

BRIEF DESCRIPTION OF THE DRAWINGS

Objectives and advantages of the invention will be described below and with reference to the accompanying drawings and illustrations, wherein the numerals and captions on different figures represent corresponding elements of the structure or design.

FIG. 1 is a schematic illustration of the prototype of the non-intrusive microwave processor. In essence it is a microwave cavity with loading and unloading doors; four klystron or magnetron microwave generators surrounding the cavity; loading and unloading tables; a 6–8 Kw microwave power generator; a process controller or programmer and a hydraulic generator. The hydraulic generator, a shredder and compactor are additions to the basic or simplified design and the inclusion of these and other complementary systems will in no way change or nullify the basic invention of non-intrusive microwave processing of infectious waste.

FIG. 2 is a schematic illustration of a semi-automatic or continuous process The moving belt conveys, loads and unloads the red bag and is an integral part of the oven cavity. The controller and programmer will automatically process the red bag throughout the loading-decontamination-unloading process.

FIG. 3A is a schematic illustration of the next stage in the development embodying the non-intrusive principle in that, unlike FIGS. 1 & 2, where the processing of a single red bag is intermittent or batch processed, the processing is in a continuous mode. The microwave cavity is at the appropriate processing temperature (power) and the red bags, enclosed in pressure boxes, are pushed through the tunnel oven. The use of a pressure box is essential in preventing ripping of the red bags as they pass along the oven. The red bags will 'slightly pressurize' within the box but will not protrude outside the box, and the walls of the box are inherently rigid (i.e., fixed in place to prevent further expansion of a bag prior to reaching its bursting point).

FIG. 3B illustrates the treatment steps of a red bag traveling through the tunnel oven of FIG. 3A.

DETAILED DESCRIPTION OF THE PREFERRED EMBODIMENTS

Figure 4A:
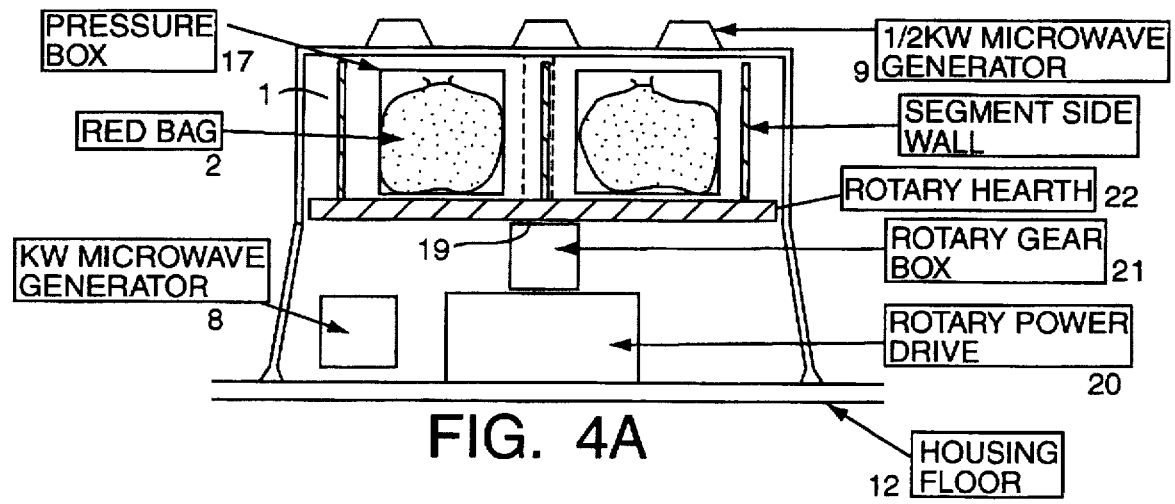
FIG. 4A schematically illustrates a partial cross-sectional, side elevational view of a rotary oven design. The advantage of the rotary oven is in its compactness and the ability for one operator to load and unload the red bags from one location.

FIG. 1 is a schematic cross-sectional view of a relatively simple or prototype model of a non-intrusive microwave decontamination machine for the processing of infectious waste in accordance with the present invention. A better understanding of the embodiment of the invention and distinguishing features of the machine may be obtained if attention is focused upon the following:

Approximately 30 lbs. of medical waste, enclosed and sealed in red bags and in temporary storage at the facility will be processed by loading into the microwave cavity 1 defined by a cavity wall. The red bag 2 contains typical medical waste as identified above and moisture, either as an intrinsic part of or intentionally added in the packing process, will sit in the base of the microwave oven. Space around and above the red bag 2 is limited by the cavity wall forming a rigid support surface that does not move if the red bag 2 should expand in volume so as to engage the rigid support surface. The space will be large enough to prevent ripping or puncturing when loading or unloading yet close enough to prevent the bag from bursting during the microwave treatment. The spacing around the bag typically defines a volume of no more than about 150% of the volume of the bag, and preferably no more than about 125% of the volume of the bag. It is anticipated that 2–3 inches will suffice as a gap between the red bag and cavity walls. After loading the microwave oven, loading door 3 is closed and locked with the locking device 4. The microwave oven unloading door 5 will be closed and locked with the locking device 4 at the time of loading. (A safety procedure is incorporated to prevent a red bag from passing through the machine without being processed.)

After the loading door 3 is locked, a process program controller 6 is activated to switch on the power to a 6–8 Kw microwave power generator 8 and electric hydraulic generator 7. The machine now is in process mode. The "Start" button is activated by the operator. The program controller 6 steadily increases power to the "processing level" (approximately 5–7 Kw or 80% of allowable power) over a time period of approximately 30 seconds. Within the red bag 2 inside the microwave cavity 1 microwaves are absorbed by water molecules, biological and other materials. The absorption is accompanied by an increase in temperature, vaporization of the water to steam, and a gradual inflation of the red bag 2 until the plastic bag touches the inner surface walls of the microwave cavity.

By 1–2 minutes, the internal environment within the red bag 2 has reached slightly supersaturated steam (approximately 105° C. to 110° C. and 1–1.25 atmospheric pressure). The above sterilizing conditions are allowed to proceed for 3–4 minutes after which time the operator (or programmer) 6 reduces the power over approximately 30 seconds.

After a further ½ minute cooling times the unloading door 5 is opened and the bag removed onto the end table. The above quoted times of temperature, steam pressure, etc. are for example only. The sterilization conditions will be defined in practice having previously been demonstrated on live but non-pathogenic bacteria. However, the times, temperatures and pressure are typical of anticipated conditions necessary for full decontamination of infectious waste.

The post-processing of the decontaminated bag will follow one or more possible routes, namely:

The processed red bag is rebagged into a green or safe processed bag, easily recognized for non-hazardous waste burial or incineration.

The use of a red bag color dye of special composition which changes from red to green upon microwaving. The dye and its use with the red bag's fabrication are additional parts of this invention.

Three to four processed red bags may be compacted into one green bag in a ready-to-incinerate manner. The recompaction will reduce the shipping volume to 20-25% of the original volume.

The decontaminated red bag may be passed through an open shredder, i.e., not within the hazardous zone of the processor. The shredded material can then be rebagged into green bags.

The decontaminated red bag and contents after shredding may be compacted into green bags.

The above outlined process is in addition, and complementary to, the non-intrusive microwave sterilization of infectious waste and has been included for completeness.

In addition to the main features of the machine defined and outlined above, the following items are identified in FIG. 1.

Hydraulic door hinges 10 are provided and driven by the electric hydraulic generator 7. In a simplified prototype proof-of-decontamination concept, the electric hydraulic generator 7 and the hydraulic door hinges 10 may be replaced by simple mechanical hinges.

An angle iron stand 11 is provided to support and house the major items of the machine and as a firm support for the loading and unloading tables (not shown).

The intended machine design will incorporate a method of transportation to the site of the medical waste generator. A transport truck floor 12 or transport raft will be an integral part of the machine, in the process of manufacture, and will be loaded and secured to the truck for transportation.

To prevent excess vibration and possible damage to the magnetrons and electronic equipment, the whole stand is supported by vibration-suppressive materials and devices such as vibro-pads 13 shown in FIG. 1.

FIG. 2 is a schematic cross-section of a semi-automatic version of the prototype microwave process shown in FIG. 1. The essential and major items are similar in both figures except for a moving belt 14 and belt drive motor 15.

The processing operation likewise will be similar except for the automatic loading and unloading of the red bags which will be conveyed into and out of the microwave processing cavity on the moving belt. The loading doors 3 and unloading doors 5 although shown opening vertically may open horizontally as a sliding door. The three methods are all variations of a common design and in no way change the intent or purpose of the invention in the creation of an enclosed cavity for microwave decontamination of infectious waste.

As identified and defined above, the internal conditions of 105°-110° C. at 1 to 1.25 atmospheres of steam pressure will not violate the pressure vessel codes. Both FIGS. 1 and 2 illustrate a design in which the microwave cavity or oven is operated in the intermittent or batchwise mode. Each and every bag is processed individually. The infectious waste, starting at room temperature and progressing to the operating conditions and down to room temperature again is decontaminated within one processing cycle. This is exemplified as the prototype version of the non-intrusive microwave process. However, FIG. 3A shows a version of the invention as a continuous processing of red bags, The major items of the prototype outlined in FIG. 1 are included save for the microwave oven cavity 1. The single intermittent cavity has been replaced by a continuous push-through type tunnel oven 1. To replace the moving belt hearth 14 shown in FIG. 2, a pushing mechanism 16 propels the red bag 2 through the oven inside pressure boxes 17. These pressure boxes 17 act as both transport containers for the red bags, preventing ripping as they pass down the tunnel oven, and as a moving-bed pressure box as the red bag inflates due to internal steam pressure. Walls of the pressure boxes 17 are inherently rigid (i.e., fixed in place to prevent further expansion of a bag prior to reaching its bursting point).

FIG. 3B illustrates the loading, processing and recycling of the pressure box 17. The red bag 2 is loaded into the pressure box 17 at step 50. The lid of the pressure box is secured at step 52 and then the red bag 2 is microwaved within the pressure box at step 57. The red bag 2 is then allowed to cool down at step 56 before being unloaded from the pressure box at step 58.

The post-processing of the red bag into green bags, compaction and/or shredding will follow in a manner similar to that described in connection with the embodiment of FIG. 2.

Additional equipment show for completion in FIG. 3A are the pusher mechanism or ram 16, heating and air conditioning 19, thermal and microwave insulation 18, and the processing pressure box 17.

Figure 4B:
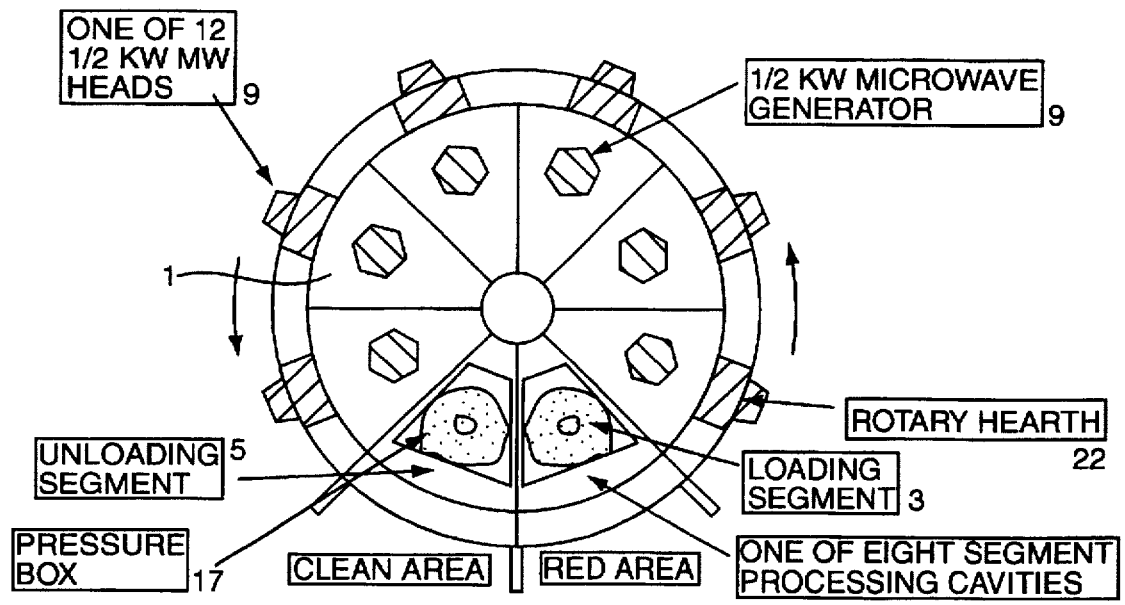
FIG. 4B schematically illustrates a top plan view of the rotary oven of FIG. 4A. The rotary oven does not require a pushing mechanism to transport the red bag through the microwave cavity. By a suitable design of the rotating doors, the "pressure box" can likewise be eliminated. The rotating segment acts as the pressure box, i.e., each segment within the rotary oven is a microwave cavity shown in FIG. 1.

As an additional variation to the non-intrusive microwave process outlined in FIGS. 1, 2, 3A and 3B, red bags containing infectious waste are processed through a procedure in which microwave energy is absorbed and in so doing converts the water within the waste to steam as shown in FIG. 3B. FIGS. 4A and 4B illustrate yet another method which includes all the salient features and embodiments of the invention.

FIGS. 4A and 4B, schematically and in Section 1, illustrate a rotary microwave oven in which the tunnel oven shown in FIG. 3A is designed to be circular and will occupy a smaller volume than the linear, or straight push-through, oven.

The oven revolves on a central spindle 19 and motor drive 20 within a circular cavity 1. Microwave magnetron heads 9 are situated above and on the side walls of the stationary part of the oven. The segments created in the rotary cavity will each pass under and past the magnetron microwave generators as the oven rotates. The red bag 2, loaded into the cavity segment, will likewise rotate through the microwave energy beam path. The design is continuous in nature; the microwave power being "on" at all times. The red bag, after processing, will be unloaded into the green area to be similarly processed as in FIG. 3A.

The design shown in FIGS. 4A and 4B illustrates the use of the pressure box in a similar manner to that shown and described in FIGS. 3A and 3B, however since the entire cavity rotates with the red bag, there is no friction between the red bag and the floor or walls of the oven. By a suitable choice of materials' design of the microwave rotary oven, the segments of the rotary cavity will be the pressure box.

As will be recognized by those of ordinary skill in the pertinent art, numerous modifications may be made to the above-described and other embodiments of the present invention without departing from the scope of the present invention as set forth in the appended claims. Accordingly, the preceding portion of this specification is to be taken in an illustrative, as opposed to a limiting sense.

I claim:

1. A method of decontaminating biomedical waste, comprising the steps of:
    A. sealing biomedical waste in an expansible container defining an internal volume and a bursting point in response to expansion of the internal volume;
    B. enclosing said container in a housing defining a volume less than the volume of said container at its bursting point;

C. subjecting said container to microwave radiation within said housing at a level and for a time sufficient to decontaminate said waste; and D. maintaining the expansible container in the sealed condition at least until the end of the period of subjecting the container to microwave radiation.

2. The method of claim 1, further comprising the step of sealing the biomedical waste in an expansible container defined by a flexible, polymeric bag at a source of generating the waste.

3. The method of claim 1 which includes the step of sealing biomedical waste in a plurality of expansible containers, transporting the plurality of containers sequentially through a tunnel; and subjecting the plurality of containers to decontaminating microwave radiation within the tunnel.

4. The method of claim 1 which includes the steps of sealing biomedical waste in a plurality of expansible containers, mounting the plurality of containers on a rotary carousel, and rotating the carousel through a microwave sterilization station for decontamination of the containers.

5. Apparatus for decontaminating biomedical waste, comprising:

A. an expansible container defining an internal volume for enclosing biomedical waste and having a bursting point in response to expansion of the internal volume;

B. a decontamination enclosure having a volume less than the internal volume of said container at its bursting point for enclosing said container therein during decontamination, and including an internal surface spaced a predetermined distance from the expansible container with the container at approximately ambient temperature, wherein (i) the predetermined distance is large enough to permit expansion of the container within the space between the internal surface and the container when the container is subjected to microwave radiation at a level and for a time sufficient to decontaminate the waste, and (ii) the predetermined distance is small enough to permit the internal surface to engage the expansible container and thereby prevent further expansion of the container prior to reaching its bursting point; and C. means for subjecting said container to microwave radiation within said decontamination enclosure at a level and for a time sufficient to decontaminate said waste.

6. Apparatus according to claim 5 wherein said decontamination enclosure defines a volume of no more than 150% of the internal volume of the expansible container.

7. Apparatus according to claim 6 wherein said decontamination enclosure defines a volume of no more than 125% of the internal volume of the expansible container.

8. Apparatus according to claim 5 including means defining an extended passageway for passage of said container sequentially therethrough while being subjected to microwave radiation therein.

9. Apparatus according to claim 5 further including a carousel for moving said container through at least one microwave decontamination station.

10. An apparatus as defined in claim 5, wherein the expansible container is defined by a flexible polymeric bag.

11. An apparatus as defined in claim 5, wherein the decontamination enclosure is defined by a housing formed of a microwave-permeable material.

12. An apparatus as defined in claim 5, wherein the decontamination enclosure defines a fixed internal volume.

13. An apparatus as defined in claim 5, wherein the predetermined distance is within the range of approximately 2 to 3 inches.

14. An apparatus for decontaminating biomedical waste, comprising:

a sealable expansible container having an internal volume defined by at least one flexible wall for receiving biomedical waste and sealing the waste within the container, and having a bursting point in response to expansion of the internal volume;

means for subjecting the expansible container to microwave radiation at a predetermined level and period sufficient to decontaminate the waste; and means for maintaining the expansible container in a sealed condition at least until the end of the period of subjecting the container to microwave radiation, said means including at least one rigid support surface spaced a predetermined distance from the at least one flexible wall when the container is at approximately ambient temperature, wherein (i) the predetermined distance is large enough to permit expansion of the expansible container within the space between the flexible wall of the container and the rigid support surface when the container is subject to microwave radiation at a level and for a time sufficient to decontaminate the waste, and (ii) the predetermined distance is small enough to permit the flexible wall of the container to engage the rigid support surface and thereby prevent further expansion of the container to reaching its bursting point.

15. An apparatus as defined in claim 14, wherein the at least one rigid support surface defines a decontamination enclosure.

16. A method as defined in claim 1, further comprising the step of adding moisture to the biomedical waste prior to sealing the waste within the expansible container.

17. A method of decontaminating biomedical waste, comprising the steps of:

sealing biomedical waste in an expansible container having an internal volume defined by at least one flexible wall, and a bursting point in response to expansion of the internal volume;

subjecting the expansible container to microwave radiation at a predetermined level and period sufficient to decontaminate the waste; and maintaining the expansible container in a sealed condition at least until the end of the period of subjecting the container to microwave radiation, the maintaining step including the step of providing at least one support surface spaced a predetermined distance from the at least one flexible wall when the container is at approximately ambient temperature, wherein (i) the predetermined distance is large enough to permit expansion of the expansible container within the space between the flexible wall of the container and the support surface when the container is subject to microwave radiation at a level and for a time sufficient to decontaminate the waste, and (ii) the predetermined distance is small enough to permit the flexible wall of the container to engage the support surface and thereby prevent further expansion of the container prior to reaching its bursting point.

* * * * *

UNITED STATES PATENT AND TRADEMARK OFFICE
CERTIFICATE OF CORRECTION

PATENT NO. : 5,792,421
DATED : August 11, 1998
INVENTOR(S) : Brian Riley

It is certified that error appears in the above-indentified patent and that said Letters Patent is hereby corrected as shown below:

In the Claims:

Claim 14, column 8
Line 31, after "container" insert --prior--.

Signed and Sealed this

Twelfth Day of January, 1999

Attest:

Attesting Officer

*Acting Commissioner of Patents and Trademarks*